United States Patent [19]

Schwarze et al.

[11] 4,390,719

[45] Jun. 28, 1983

[54] 1-METHYL-2-CHLOROCYCLO-PROPANECARBOXYLIC ACID AND ITS ESTER

[75] Inventors: Werner Schwarze, Frankfurt; Axel Kleemann, Hanau; Wolfgang Leuchtenberger, Bruchkobel, all of Fed. Rep. of Germany

[73] Assignee: Degussa Aktiengesellschaft, Frankfurt, Fed. Rep. of Germany

[21] Appl. No.: 280,356

[22] Filed: Jul. 6, 1981

[30] Foreign Application Priority Data

Jul. 10, 1980 [DE] Fed. Rep. of Germany ....... 3026093

[51] Int. Cl.³ .................... C07L 61/04; C07L 69/74
[52] U.S. Cl. .................................. 560/124; 71/118; 562/506; 564/190
[58] Field of Search .......................... 560/124; 562/506

[56] References Cited

U.S. PATENT DOCUMENTS

| 2,996,536 | 8/1961 | Carbon | 560/124 |
| 3,856,976 | 12/1974 | Hunter | 560/124 |

FOREIGN PATENT DOCUMENTS

| 2077 | 5/1979 | European Pat. Off. | 560/124 |
| 2802967 | 7/1978 | Fed. Rep. of Germany | 560/124 |

OTHER PUBLICATIONS

Reinecke, J. Org. Chem. 29, pp. 299–304, (1964).
Hofmann, J. Am. Chem. Soc. 81, pp. 992–997, (1959).

Primary Examiner—Michael L. Shippen
Attorney, Agent, or Firm—Cushman, Darby & Cushman

[57] ABSTRACT

1-Methyl-2-chlorocyclopropanecarboxylic acid and its lower esters are produced by the selective hydrogenating dechlorination of the corresponding 1-methyl-2,2-dichlorocyclopropane compounds. The new materials can be used as intermediate products for the production of pesticides and medicines.

3 Claims, No Drawings

1-METHYL-2-CHLOROCYCLOPROPANECARBOXYLIC ACID AND ITS ESTER

BACKGROUND OF THE INVENTION

Cyclopropanecarboxylic acids are important intermediate products for the production of pesticides and pharmaceuticals. Their esters can be used as miticides (German AS No. 2417372, the entire disclosure of which is hereby incorporated by reference and relied upon). 1-Methylcyclopropylcarboxanilido derivatives can be used as selective herbicides in the cultivation of soybeans (Pilgram U.S. Pat. No. 4,168,153 the entire disclosure of which is hereby incorporated by reference and relied upon).

4-Amino-6-(1-methylcyclopropyl)-3-methylthio-1,2,4-trizin-5-one represents a highly effective herbicide (Belgian Pat. No. 869138). For its synthesis there is needed 1-methylcyclopropanecarboxylic acid.

Other cyclopropanecarboxylic acids, e.g. 2-(2,2-dihalovinyl)-3,3-dialkyl cyclopropanecarboxylic acid and its ester are important key materials for the synthesis of a group of compounds which are known under the designation "synthetic pyrethroids" and which have noteworthy insecticide and acaricide activity.

SUMMARY OF THE INVENTION

The object of the present invention is the development of a new cyclopropanecarboxylic acid, namely 1-methyl-2-chlorocyclopropanecarboxylic acid, as well as its esters. These compounds correspond to the general formula

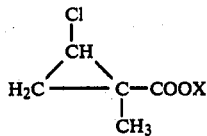

in which X stands for a hydrogen atom or a branched or straight chain alkyl group having 1-6 carbon atoms.

These compounds are characterized by the fact that in contrast to the unsubstituted cyclopropanecarboxylic acids or esters they have a stable cyclopropane ring, which e.g. is not splittable by acids. The new compounds can be produced according to the invention from compounds of the general formula

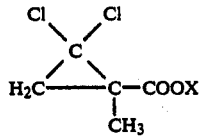

in which X is a hydrogen atom or a branched or straight chain alkyl group having 1-6 carbon atoms by selective hydrogenation in the presence of a noble metal catalyst and in the presence of an HCl acceptor and in a given case in the absence of a solvent. Hereby if one starts from the free acid then it is necessary to first convert this into salt form, e.g. the sodium or potassium salt.

The 1-methyl-2,2-dichlorocyclopropanecarboxylic acid esters can be produced in very high yields from methacrylic acid esters and chloroform in the presence of high strength alkalis, e.g. NaOH or KOH, and in the presence of a phase transfer catalyst, e.g. triethylbenzyl ammonium chloride (E. V. Dehmlow, Leibigs Ann. Vol. 758 pages 148–152 (1972)). The thus obtained esters can easily be saponified with alkali without destruction of the cyclopropane ring.

The selective hydrogenation dechlorination of the invention can be carried out in water, watersolvent mixtures, e.g. in methanol, ethanol, n-propanol, i-propanol, n-butanol, i-butanol, sec.-butanol, t-butanol, dioxane and tetrahydrofurane. However, it is also possible to operate under water free (anhydrous) conditions if one starts from the liquid esters and employs anhydrous ammonia as the HCl-acceptor. Preferably the procedure is carried out in water as well as in methanol or ethanol or in mixtures of these.

The hydrogenation catalysts used in the invention are known. For example their production is described in Adams et al, J. Amer. Chem. Soc. Vol. 45 pages 2175–2178 (1923). The technique of the production of precipitation and impregnation as well as soaking catalyst is described in detail in Ullmann, 4th edition Vol. 13 on page 558 et seq.

For this purpose there are particularly used the noble metals platinum and palladium. However, there are preferably used palladium catalysts on carriers, especially on activated carbon. As further examples of carrier materials there can be used silica gels, kieselguhr, alumina, zeolites, pumice as well as various silicates. Among these catalyst Raney-nickel is not preferred.

As HCl acceptors there can be particularly used aqueous solutions of sodium hydroxide and potassium hydroxide or ammonia. Further there can be used lithium hydroxide, sodium bicarbonate potassium bicarbonate, lithium bicarbonate, sodium carbonate, potassium carbonate and lithium carbonate and the carbonates of alkaline earth metals, e.g. calcium carbonate, magnesium carbonate, strontium carbonate and barium carbonate, alkaline earth bicarbonates, e.g. calcium bicarbonate and magnesium bicarbonate, alkaline earth hydroxides, e.g. calcium hydroxide, barium hydroxide, organic tertiary amines, e.g. trimethyl amine, triethyl amine, ammonia, ammonium bicarbonate and ammonium carbonate. In water free operation there can be used alcoholates, especially sodium methylate or sodium ethylate or anhydrous ammonia. Preferably there is employed sodium methylate.

In carrying out the process of the invention if the starting material is free 1-chloro-2,2-dichlorocyclopropanecarboxylic acid then it is necessary to first convert this into salt form, e.g. as the sodium salt, as for example can take place using alkali in known manner. It is of course understood that in this case there must be used for the dehydrogenating dechlorination an additional mole of the HCl acceptor per mole of acid. There can be used tertiary organic amines both in normal solvents as well as in water as HCl acceptors. For example the free starting acid, e.g. in water with triethyl amine can be converted into the salt form and triethyl amine used again as the HCl acceptor. However, there can also be used mixtures of organic tertiary amines and inorganic alkalis. It is suitable to employ the HCl acceptor in a slight excess of, for example, 10%.

If in carrying out the process of the invention there are employed starting materials of general formula (II) in which X is an alkyl group, thus there are used esters as starting materials, then it is suitable to use ammonia as the HCl acceptor. This can be employed either as an aqueous solution or in water free form. In both cases no saponification takes place during the hydrogenation and also there is no conversion into the amide.

The hydrogenation dechlorination can be carried out at pressures between 10 and 250 bar, preferably at pressures of 50 to 150 bars.

Furthermore the hydrogenation can be carried out between 20° and 120° C., preferably 50° and 80° C.

The new compounds of formula (I) are colorless, distillable oils. In every case they are cis-trans-isomers.

In formulae (I) and (II) X can stand for hydrogen, methyl, ethyl, n-propyl, i-propyl, n-butyl, sec-butyl, i-butyl, t-butyl, n-pentyl, i-pentyl, n-hexyl, 1-methylpentyl and 2-methylpentyl. Specific examples of compounds within the invention include 1-methyl-2-chlorocyclopropanecarboxylic acid, 1-methyl-2-chlorocyclopropanecarboxylic acid methyl ester, 1-methyl-2-chlorocyclopropanecarboxylic acid ethyl ester, 1-methyl-2-chlorocyclopropanecarboxylic acid isopropyl ester, 2-chlorocyclopropanecarboxylic acid t-butyl ester, 2-chlorocyclopropanecarboxylic acid sec-butyl ester, 2-chlorocyclopropanecarboxylic acid n-hexyl ester.

The new materials can be employed as intermediate products for the production of pesticides and medicines. Thus for example they can be converted into 1-methyl-2-chlorocyclopropanecarboxylic acid chloride (in a manner analogous to that described in Pilgram U.S. Pat. No. 4,168,153) and then reacted with a 4-(alkyl or dialkylamino)-3-(trifluoromethyl) benzamine, e.g. 4-(isopropylamino)-3-trifluoromethyl) benzamine, to form the corresponding carboxanilide, e.g., 4'-(isopropylamino)-3'-(trifluoromethyl)-1-methyl-2-chlorocyclopropanecarboxanilide in the manner described in the Pilgram patent. The carboxanilides can be used as pre-emergent and post-emergent herbicides in the manner disclosed in Pilgram, e.g. to kill weeds such as wild mustard and pigweed.

Also the compounds can be reacted in the manner described in German OS No. 2417372, e.g. Examples 1, 2 and 3 thereof to form miticides. The miticides can be used as described in the German OS No. 2417372.

The process can comprise, consist essentially of or consist of the stated steps with the recited materials.

Unless otherwise indicated all parts and percentages are by weight.

EXAMPLE 1

934 grams of 1-methyl-2,2-dichlorocyclopropanecarboxylic acid methyl ester (98% corresponding to 5 moles) were dropped into a solution of 225 grams of KOH in 1800 ml of CH$_3$OH within one hour thereby the temperature should not exceed 30° C. After 4 hours the saponification was ended, then the methanol was distilled off and the composition correspondingly made up with water (1800 ml). To this colorless solution there was added again with cooling 225 grams of solid KOH, 50 grams of Pd on activated carbon (5%) added, and the entire mixture transferred into a 5 liter autoclave, this was closed and pressured to 50 bar with hydrogen. Reaction temperature is 50° C. The hydrogenation was ended in 6 hours. The autoclave was emptied. The solution filtered off from the catalyst and the solution cooled to 10° C. Then there were added 1.5 liters of methylene chloride. Then under good cooling between 5° C. and 15° C. there was added concentrated (38%) HCl and the pH adjusted to 1. The methylene chloride layer was separated off, dried and distilled in a column (1 meter, wire mesh).

1-Methyl-2-chlorocyclopropanecarboxylic acid distilled at B.P.$_4$ 114°–115° C.

Analysis: C$_5$H$_7$ClO$_2$ (Mol-Wt. 134.5)

Calculated C: 44.6; H: 5.2; Cl: 26.2; Found C: 44.8; H: 5.3; Cl: 25.9.

Amount: 525.2 grams corresponding to 78.1% of theory. NMR and GC analysis showed that the acid is a cis-trans mixture (89:11).

EXAMPLE 2

732 grams of 1-methyl-2,2-dichlorocyclopropanecarboxylic acid methyl ester (4 moles) were mixed with 400 ml of methanol. The mixture was placed in a 5 liter autoclave, 18 grams of Pd on activated carbon (5%) added and the autoclave closed. Then it was pressured with 136 grams of ammonia (200 ml NH$_3$), and subsequently with hydrogen to a total pressure of 100 bar. The hydrogenation started at 60° C., it was over in 5 hours. The autoclave was opened, the solution filtered and first concentrated in a vacuum and suctioned off with pressure from NH$_4$Cl. The residue was rectified in a vacuum in a 1 meter Raschig column.

The 1-methyl-2-chlorocyclopropanecarboxylic acid methyl ester distilled at B.P.$_{12}$ 57°–16° C.

Analysis: C$_6$H$_9$ClO$_2$ (Mol-Wt. 148.5)

Calculated C: 48.5; H: 6.1; Cl: 23.8; Found C: 48.5; H: 6.0; Cl: 23.6.

Amount: 482.3 grams, corresponding to 81.2% of theory. The ester is a cis-transmixture (NMR and GC analysis).

EXAMPLE 3

450 grams of 1-methyl-2,2-dichlorocyclopropanecarboxylic acid n-butyl ester (2 moles) were placed in a 2 liter autoclave, 400 ml of concentrated aqueous ammonia (about 25%, about 4 moles) were added and 10 grams of Pd on activated carbon added, the autoclave closed, pressured to 100 bar of H$_2$ and heated. At 50° C. the hydrogenation started, it was finished in 4 hours. The product was filtered. The aqueous solution was separated and distilled. 1-Methyl-2-chlorocyclopanecarboxylic acid butyl ester has a B.P.$_{12}$ 99°–100° C.

Analysis: C$_9$H$_5$ClO$_2$ (Mol-Wt. 190.5)

Calculated C: 56.7; H: 7.9; Cl: 18.6; Found C: 56.6; H: 7.8; Cl: 18.4.

Amount: 305.6 grams, corresponding to 80.2% of theory.

EXAMPLE 4

There was dissolved 338 grams of crystalline 1-methyl-2-2-dichlorocyclopropanecarboxylic acid in 166 grams of NaOH plus 1 liter of water, everything was placed in a 2 liter autoclave, 10 grams of Pt on activated carbon added, the autoclave closed, pressured with H$_2$ to 100 bar and hydrogenated at 50°–60° C.

The working up was carried out as described in the preceding examples and yielded 211.2 grams of 1-methyl-2-chlorocyclopanecarboxylic acid corresponding to 78.5% of theory.

EXAMPLE 5

There were dissolved in 1 liter of water 382 grams of 1-methyl-2,2-dichlorocyclopropanecarboxylic acid sodium salt (=2 moles), there were added 88 grams of NaOH and 5 grams of PtO$_2$ and the entire mixture placed in a 4 liter autoclave. The autoclave was closed and pressured to 100 bar with H$_2$. The hydrogenation was carried out between 60° and 75° C. It was finished in 6 hours.

The customary working up yielded 212.8 grams of 1-methyl-2chlorocyclopropanecarboxylic acid, B.P.$_{14}$ 113°–116° C. Yield: 79.1% of theory.

EXAMPLE 6

There were placed in a 2 liter autoclave 253 grams of 1-methyl-2,2-dichlorocyclopropanecarboxylic acid n-hexyl ester, 200 ml of methanol and 10 grams of palladium on activated carbon (10%) added, the autoclave closed and pressured with 100 grams of ammonia.

Hydrogen was impressed (100 bar) and the mixture heated to 80°–90° C. The hydrogenation was ended in 6 hours. The contents of the autoclave were placed in 2 liters of water and shaken with methylene chloride. After driving off the solvent the solution was distilled in a vacuum. B.P.$_{17}$ 132.5°–133.5° C.

Analysis: $C_{11}H_{19}O_2Cl$ (Mol-Wt. 218.5)

Calculated C: 60.4; H: 8.7; Cl; 16.2; Found C: 60.3; H: 8.5; Cl; 16.0.

Yield of 1-methyl-2-chlorocyclopropanecarboxylic acid n-hexyl ester: 180.5 grams corresponding to 82.6% of theory.

What is claimed is:

1. A 1-methyl-2-chlorocyclopropane compound of the formula

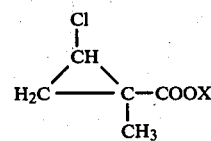

in which X is a hydrogen atom or a 1–6 carbon atom alkyl group.

2. A compound according to claim 1 where X is hydrogen.

3. A compound according to claim 1 where X is a 1–6 carbon atom alkyl group.

* * * * *